(12) United States Patent
Enayati

(10) Patent No.: US 6,290,701 B1
(45) Date of Patent: Sep. 18, 2001

(54) BIOABSORBABLE RIVET BONE FASTENER

(76) Inventor: Albert Enayati, 809 Carter La., Paramus, NJ (US) 07652

(*) Notice: Subject to any disclaimer, the term of this patent is extended or adjusted under 35 U.S.C. 154(b) by 0 days.

(21) Appl. No.: 09/482,444

(22) Filed: Jan. 11, 2000

(51) Int. Cl.$^7$ ............................. A61B 17/86; A61B 17/70
(52) U.S. Cl. ................................................ 606/72; 606/68
(58) Field of Search .................... 606/68, 72, 67

(56) References Cited

U.S. PATENT DOCUMENTS

| | | | |
|---|---|---|---|
| 2,490,364 | * 12/1949 | Livingston | 606/68 |
| 2,699,774 | * 1/1955 | Livingston | 606/68 |
| 3,805,775 | * 4/1974 | Fischer et al. | 606/68 |
| 5,441,500 | * 8/1995 | Seidel et al. | 606/68 |
| 5,489,210 | * 2/1996 | Hanosh | 606/72 |
| 5,713,903 | * 2/1998 | Sander et al. | 606/72 |
| 5,968,044 | * 10/1999 | Nicholson et al. | 606/72 |

\* cited by examiner

*Primary Examiner*—Paul J. Hirsch
(74) *Attorney, Agent, or Firm*—Michael G. Petit

(57) ABSTRACT

Bone fasteners consisting of a rivet and an expansion pin for attaching soft tissue and bone plates to bone. The rivet has an enlarged proximal end, a tubular body portion dimensioned to fit snugly within a hole drilled in a bone, and a distal end having expandable legs. The expansion pin is either slidably or rotatably mounted within an axial bore in the rivet. In a first embodiment, the expansion pin has a metallic traction portion and a conical, preferably bioabsorbable, distal end portion releasably affixed thereto. In use, the rivet is inserted into a pre-drilled hole in a bone. When tension is applied to the traction portion of the expansion pin, the conical end portion progressively advances into the bore thereby forcing the legs on the distal end of the rivet to expand outwardly. When the legs are fully expanded, further progress of the conical portion is arrested by a shoulder stop within the axial bore. Further tension on the traction portion breaks the expansion pin, leaving the conical distal end within the expanded bore. In a second embodiment, a conical expansion pin is pressed into the rivet's axial bore from the proximal end of the bore. In a particularly preferred embodiment, rotation of an expansion pin housed within the rivet's axial bore exerts an outwardly directed force on the legs. When the legs are sufficiently expanded, a groove detent within the bore resists further rotation of the expansion pin. All embodiments of the rivet bone fasteners can be adapted for compression reduction of a fracture. With all embodiments of the bone fasteners, both the rivet and the expansion pin, or portions thereof, may be fabricated from either bioabsorbable or nonabsorbable materials, the choice of material depending on the application.

14 Claims, 4 Drawing Sheets

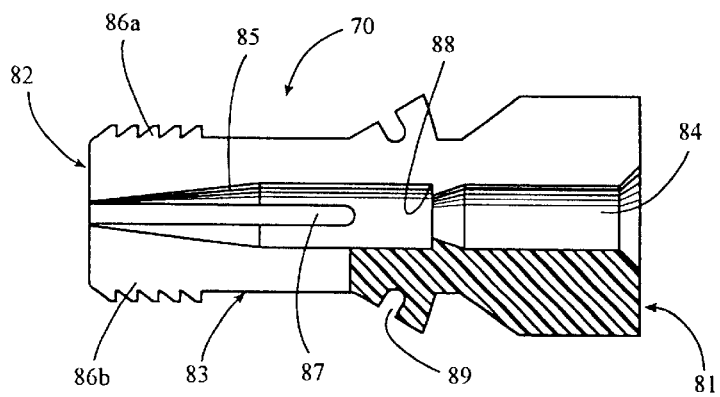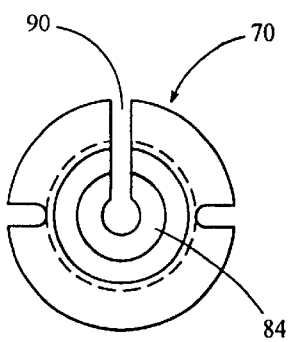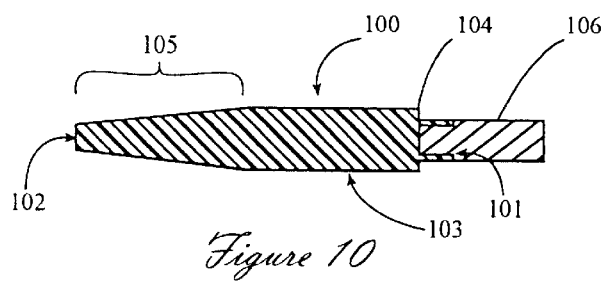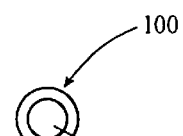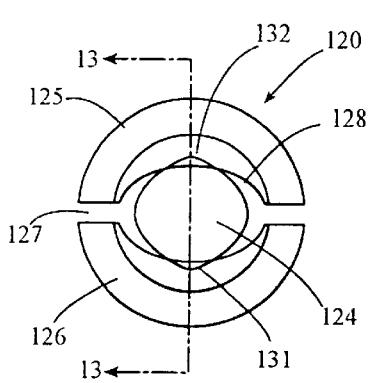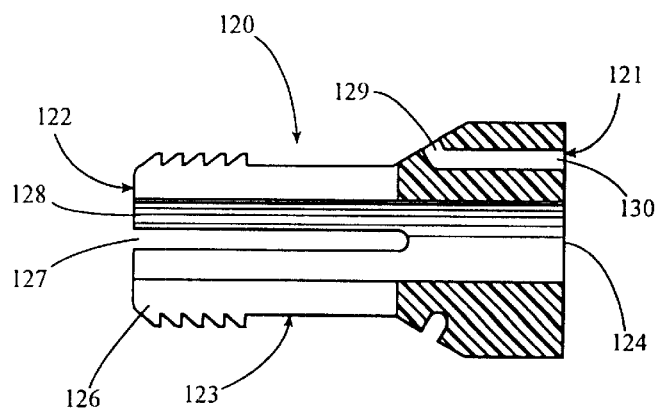

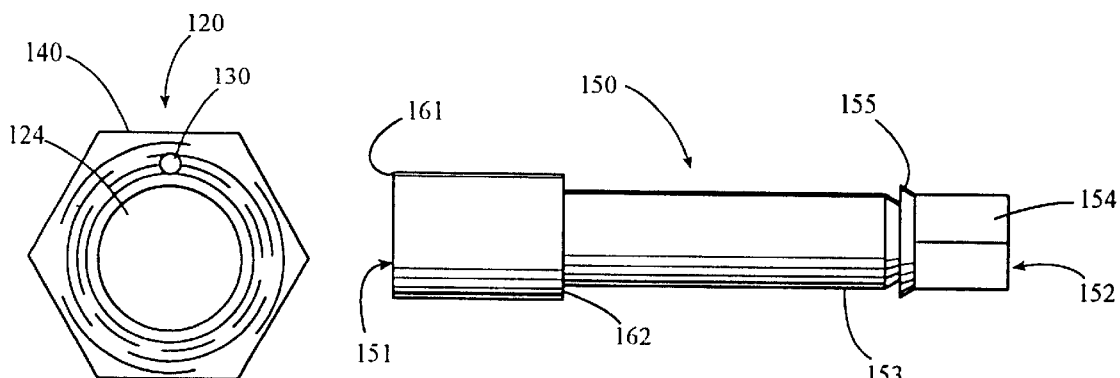
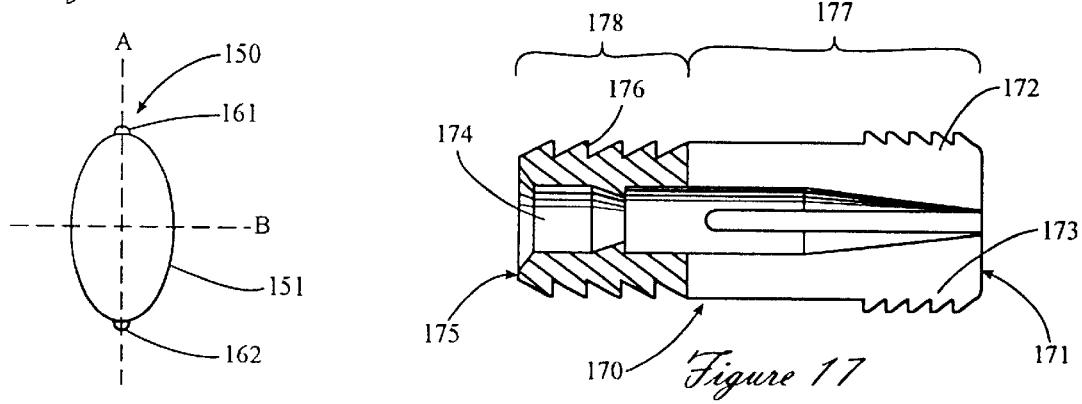
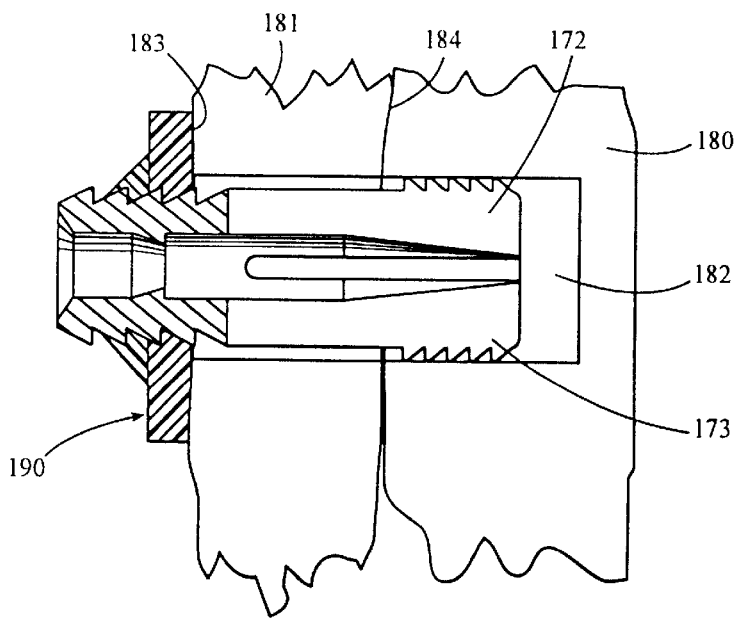

BIOABSORBABLE RIVET BONE FASTENER

BACKGROUND OF THE INVENTION

1. Field of the Invention

This invention relates to fasteners for attaching a substrate to a bone, and more particularly to fasteners for anchoring soft tissue or bone plates to bone.

2. Prior Art

Both bioabsorbable and nonbioabsorbable bone fasteners adapted for attaching bone plates and soft tissue, such as, for example tendons and ligaments, to bone are known in the art. Such prior art fasteners include staples and tacks, screws, and rivets. Examples of staple type fasteners are illustrated in U.S. Pat. Nos. 4,454,875 and 4,570,623. Such bone staples generally include barbs on the cross-member which are useful for securely grasping a soft tissue such as a ligament and attaching it to bone.

The second type of fasteners include both screws and screw-washer combinations wherein a hole must be drilled in a bone for the purpose of receiving the screw. Screws may be fabricated from a surgically acceptable, biocompatible metal such as titanium, stainless steel or a cobalt-chromium alloy. Such metallic screws may be self-tapping. In bone fasteners comprising a screw-washer combination, the washer has spikes on one surface operable for grasping tissue, and a central aperture through which the screw is inserted into a bone. If the screw is fabricated from a bioabsorbable material, the hole in the bone must be tapped before the screw can be urged thereinto. Other ligament anchoring systems are disclosed in U.S. Pat. Nos. 4,927,421 and 4,870,957.

The staple and screw types of bone fastening devices possess several disadvantages. For example, staples, which are meant to be hammered into bone, must be made of a strong material, such as a metal. The use of staples is time consuming, traumatic and precludes the use of bioabsorbable polymers as suitable material for staple-type fasteners. As with staples, until such time as stronger and harder bioabsorbable materials become available, self-tapping screws must comprise a biocompatible metal. Both regular and self-tapping screw fasteners require a hole be drilled in the bone prior to use, If the screw comprises a non-metallic bioabsorbable material, the hole must also be tapped in order to receive the screw which requires an additional time consuming step.

In accordance with current art, metallic staples and screw fasteners are either permanently implanted within a bone, or a second surgical operation must be performed in order to remove them. In either case, implantation of metal fasteners does not allow for the gradual transfer of stress back to the bone/soft tissue junction as the healing proceeds. This, in turn, may slow down or impede the healing process. Furthermore, metal screws and staples may migrate from their original site of implantation over a period of time and lodge in a tissue causing pain. Permanently implanted metallic screw and staple fasteners can even migrate from the site of implantation to lodge within a joint, creating significant damage to articulator cartilage and other structures.

To overcome the disadvantages of the screw and staple types of bone fasteners, expandable rivets, both bioabsorbable and metallic, have been developed. Examples of such rivets are disclosed in U.S. Pat. Nos. 5,968,044; 5,911,721; and 5,725,529 to Nicholson et al., and U.S. Pat. No. 5,720,753 to Sander et al. Such rivets, which are either bioabsorbable or metallic, have the advantage that they may be inserted into an untapped hole, thereafter to be expanded, thereby reducing the time required for implantation of the rivets. Prior art rivets include an elongate body portion having an axial bore, an expanded head portion and an expandable leg portion. All of the prior art rivet-type bone fasteners include an expansion pin slidably mounted within the axial bore of the rivet. The bore and a portion of the expansion pin are configured such that movement of the expansion pin in an axial direction forces apart two or more legs on the rivet. The outer surface of the legs is adapted to engage the surrounding bone thereby preventing the rivet from backing out of the hole following implantation. The rivets include means for fastening a substrate to the rivet.

The expansion pins or functionally similar slidable elements used to expand the legs of the rivet bone fasteners, in accordance with the prior art, include a break-away portion which is not implanted in the bone with the rivet. On certain embodiments of the prior art rivets, tension must be applied to the expansion pin in order to expand the legs of the rivet. The tensile strength required to separate the traction portion of the expansion pin from the conical end portion may vary. Such tension may either pull the rivet out of the hole or cause the expansion pin to break prematurely. so that the security of the rivet within the bone is compromised.

Conversely, in other embodiments of the prior art rivets, the expansion pin is advanced into the rivet's axial channel in a distal direction (ie: deeper into the hole) to expand the legs. The expansion pin is urged into the axial channel by means of an insertion tool which is affixed to the expansion pin by frangible means. In the event that the insertion tool prematurely breaks away from the expansion pin, the rivet may not be securely anchored within the hole and prove difficult to remove. Accordingly, there remains a need for a fastener for securing tissue to bone which will have a predictable and sufficient initial anchorage strength to permit gradual load sharing to provide full repair and restoration of function of the tissue and bone. There exists a further need for a fastener device which is easily and rapidly attached to tissue and can be reliably anchored into bone which will not pull out of the bone or migrate from its original position following implantation.

SUMMARY OF THE INVENTION

Rivet bone fasteners are provided in accordance with the present invention which are operable for attaching either an autogenous substrate such as tissue, or an exogenous substrate such as a bone plate, to a bone. Embodiments of the rivet bone fasteners are adapted to meet the variety of demands presented by various surgical procedures employed during orthopedic, plastic and reconstructive surgery. The rivet bone fasteners of the present invention include absorbable, nonabsorbable and hybrid embodiments.

It is a first object of the invention to provide a device which may be used to attach a material substrate to a bone.

It is a further object of the invention to provide a bone fastener device which may be anchored securely in an untapped hole drilled in a bone.

It is another object of the invention to provide a bone fastener device meeting the above objectives which may be permanently implanted in a bone and which will remain anchored in bone after implantation.

It is yet a further object of the invention to provide a bone fastener which may be either non-absorbable, partially absorbable or totally absorbed by the body following implantation therein.

It is yet another object of the invention to provide a rivet bone fastener adapted for insertion into a hole in a bone, thereafter to be expanded to provide non-releasable engagement of the rivet with the wall of the hole.

The features of the invention believed to be novel are set forth with particularity in the appended claims. However the invention itself, both as to organization and method of operation, together with further objects and advantages thereof may be best be understood by reference to the following description taken in conjunction with the accompanying drawings in which:

BRIEF DESCRIPTION OF THE DRAWINGS

FIG. 8 is a elevational cross-sectional view, taken along section line 8—8 of FIG. 7, illustrating a top-loading embodiment of a rivet bone fastener in accordance with the present invention.

FIG. 9 is a proximal end view of the rivet bone fastener of FIG. 7.

FIG. 10 is a cross-sectional elevational view of a top loading expansion pin adapted for use with the rivet bone fastener of FIG. 7.

FIG. 11 is a proximal end view of the top loading expansion pin of FIG. 10.

FIG. 12 is a distal end view of a particularly preferred embodiment of a rivet bone fastener shown in further detail in FIG. 13.

FIG. 13 is a longitudinal cross-sectional view, taken along section line 13—13 of FIG. 12 illustrating a particularly preferred embodiment of a bone rivet in accordance with the present invention wherein the legs comprising the rivet are expanded by means of a rotational expansion pin.

FIG. 14 is a proximal end view of the rivet of FIGS. 12 and 13.

FIG. 15 is a longitudinal elevational view of a rotatable expansion pin in accordance with the present invention adapted for use with the rivet of FIG. 12.

FIG. 16 is a distal end view of the expansion pin of FIG. 15.

FIG. 17 is a cross-sectional side view of a bone compression rivet in accordance with the present invention.

FIG. 18 is a cross-sectional view of a bone fracture site illustrating the use of a compression rivet and a compression washer to stabilize and compress the fracture site.

DESCRIPTION OF THE PREFERRED EMBODIMENTS

Figure 1:
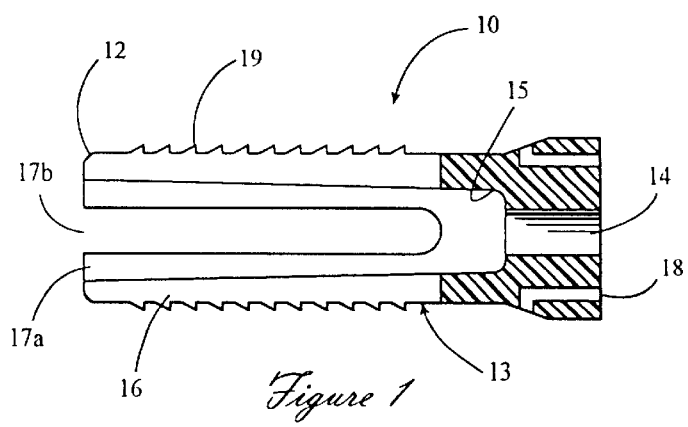
FIG. 1 is a cross-sectional view of a rear loading rivet bone fastener in accordance with the present invention.
Figure 2:
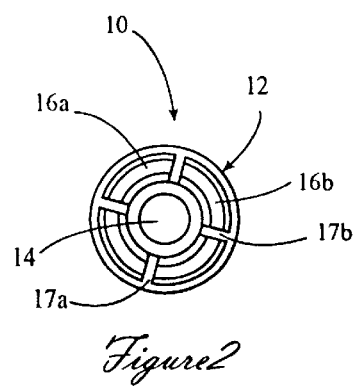
FIG. 2 is a end view of the distal end of the rivet bone fastener of FIG. 1.
Figure 3:
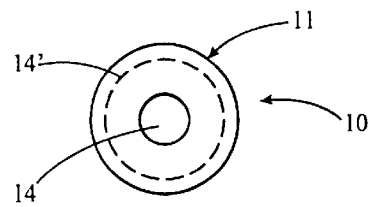
FIG. 3 is a end view of the proximal end of the rivet bone fastener of FIG. 1.

The term "bioabsorbable material" or "bioabsorbable", as used herein, means that the referenced material is biocompatible, and that at least a portion of the material is either excreted or assimilated by the body following implantation therewithin. Turning now to FIG. 1, a expandable, rear-loading rivet bone fastener 10 has a proximal head portion 11, a distal end 12 and a body portion 13 therebetween. The rivet bone fastener 10 has an interior cylindrical bore 14 coextensive with the length thereof having a shoulder 15 therewithin. The distal portion 12 of the body portion 13 includes at least two expandable legs 16a and 16b (only one leg 16a is shown in FIG. 1 due to the cross-sectional view) having at least one slot 17a therebetween. In the embodiment of the rivet shown in FIG. 1, there are an additional pair of expandable opposing legs separated by slot 17b. The cylindrical bore 14 tapers outwardly between the shoulder 15 and the distal end 12 forming a conical aperture 14' in the distal end 12 which is coaxial and concentric with the axial bore 14. The distal end 12 and the proximal end 11 of the rivet 10 are shown in end view, in the direction of the axial bore 14, in FIGS. 2 and 3 respectively.

Figure 4:
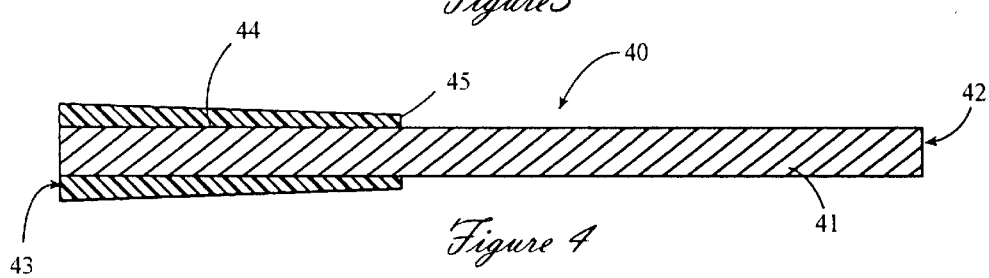
FIG. 4 is a longitudinal cross-sectional view of a rear loading expansion pin used to expand the rivet bone fastener of FIG. 1.
Figure 5:
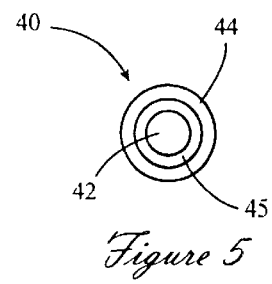
FIG. 5 is a distal end view of the expansion pin of FIG. 4.

An expansion pin 40 for use with the rear-loading rivet 10 described above, is shown in longitudinal cross-sectional view in FIG. 4. The expansion pin 40 comprises an elongate cylindrical core 41, preferably a length of a metallic wire, having a proximal end 42 and a distal end 43. The distal end 43 of the core 41 is surrounded by a conical expander portion 44 having an abrupt shoulder 45 on the proximal end thereof. The conical expander portion 45 comprises a structural material which is different from the structural material comprising the core 41, and is most preferably a bioabsorbable material. Suitable materials for fabricating the conical expander portion 44 include polymer blends of glycolide and/or lactide homopolymer, copolymer and/or glycolide/lactide copolymer and polycaprolactone copolymers, and/or copolymers of glycolide, lactide, poly(L-lactide-co-DL-lactide), caprolactone, polyorthoesters, polydioxanone, trimethylene carbonate and/or polyethylene oxide or any other bioabsorbable material. The outer surface of the conical expander portion may comprise means for positively engaging the wall of the rivet's axial bore 14 in order to prevent backward motion of the expansion pin within the axial bore. A right end-on view of the conical expansion pin 40 is shown in FIG. 5.

Figure 6:
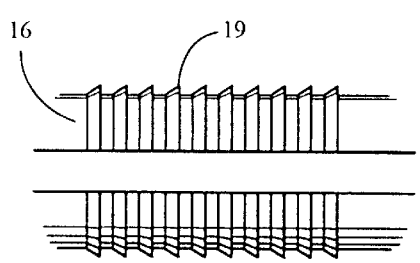
FIG. 6 is an enlarged view of the outer surface of the rivet bone fastener of FIG. 1 illustrating a modification of the outer surface of the rivet for securely gripping a bone.
Figure 19:
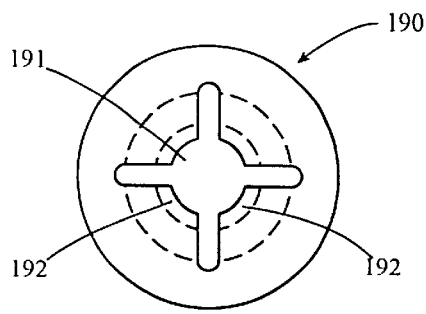
FIG. 19 is a top view of a compression washer adapted for use with the compression rivet of FIG. 17.
Figure 20:
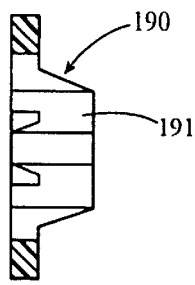
FIG. 20 is a cross-sectional view, taken along section line 20—20 of FIG. 19, illustrating the locking flanges adapted to lockingly engage a compression rivet.

In order to use a rivet type of bone fastener in accordance with the present invention, a hole is first drilled in a bone at a site where a substrate such as soft tissue or a bone plate is to be attached. The core 41 of the expansion pin 40 is dimensioned to slidably fit within the axial bore 14 of the rivet 10. The proximal end 42 of the expansion pin 40 is inserted into the distal end 12 of the axial bore 14 in the rivet 10 and urged thereinto until the conical portion of the expansion pin is snugly lodged within the axial bore and cannot be further advanced without expanding the legs 16 of the rivet. The distal end 12 of the rivet is inserted into the hole and advanced until the proximal head end 11 is adjacent the bone or bone plate and the rivet can be advanced into the hole no further. With the head of the rivet held firmly against the bone or a bone plate, tension is applied to the proximal end 42 of the core thereby urging the conical portion deeper into the axial bore and expanding the legs 16 outwardly into contact with the surrounding bone. When the shoulder 45 of the conical expansion portion 44 abuts the shoulder 15 in the rivet's axial bore 14, the conical portion can advance no further and the core 41 of the expansion pin breaks away from the conical expansion portion leaving the expanded rivet held securely in the hole. The outer surface 19 of the legs of the rivet may be modified, as shown in FIG. 6, to provide a positive attachment of the rivet to the bone. A suture 18 (FIG. 1) or a washer 190 (FIGS. 18–20) connected to the head, neck, or another part of the rivet, may be used to securely affix a substrate to the head of the rivet and hence, the bone.

Figure 7:
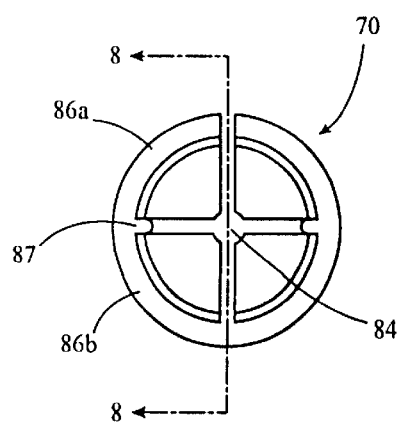
FIG. 7 is a distal end view of the top-loading embodiment of a rivet bone fastener shown in further detail in FIGS. 8 and 9.

The rivet bone fastening device 10, described in FIGS. 1–6, can be adapted to receive an expansion pin which is inserted through the proximal end of the axial bore. Such an embodiment, referred to herein as a "top-loading" rivet bone fastener, is indicated at numeral 70 in FIGS. 7, 8 and 9. FIG. 7 is a distal end view of the top-loading rivet 70 in accordance with the present invention. FIG. 8 is a elevational cross-sectional view, taken along section line 8—8 of FIG. 7, illustrating the top-loading embodiment of a rivet bone fastener. The top-loading rivet 70 has a proximal head end 81, a distal end 82, and a body portion 83 therebetween. The rivet 70 has a cylindrical axial bore 84 coextensive with the length thereof, a portion of the axial bore being tapered inwardly in the distal axial direction to form a conical axial bore 85. The body portion 82 of the rivet 70 includes at least two expandable legs, 86a and 86b, symmetrically disposed in opposition to one another with respect to the axial bore, and separated by one or more slots 87. A portion of the axial bore 84 proximal to the conical axial bore 85 is constricted to form a shoulder detent 88. The body portion of the rivet may further include a circumferential groove 89 or similar means operable for attaching a suture to the rivet. A slot 90 in the body portion of the rivet 70, illustrated at numeral 90 in the proximal end view of the rivet shown in FIG. 9, enables elastic deformation of the body portion of the rivet when an expansion pin 100 is inserted into the proximal end of the rivet and advanced through the axial bore 84.

An expansion pin 100 adapted for use with the top-loading rivet 70 is illustrated in cross-sectional view in FIG. 10. The expansion pin 100 is a cylindrical member having a proximal end 101, a distal end 102 and a body portion 103 therebetween. A metallic extension portion 106, affixed to the proximal end 101 of the expansion pin 100, provides means for grasping and manipulating the expansion pin for insertion into the axial bore 84 of the top-loading rivet 70. After the expansion pin 100 has been expanded within a hole drilled in a bone, the extension portion 106 of the expansion pin is preferably removed from the pin. The body portion 103 has a circumferential shoulder 104 near the proximal end thereof. A proximal end view of the expansion pin 100 is shown in FIG. 11. A portion 105 of the body portion 103 of the expansion pin 100 near the distal end thereof, is tapered inwardly to present a smooth conical outer surface.

The proximal end of either the rivet or the expansion pin further includes substrate fastening means such as, for example, a length of either absorbable or non-absorbable suture affixed thereto.

In order to use the top-loading fastener 70 to attach a substrate such as soft tissue or a bone plate to a bone, a hole dimensioned to receive the body portion of the rivet is drilled into the bone. The distal end 82 of the rivet 70 is inserted into the hole and the rivet is urged inwardly until the rivet can be advanced no further. The distal end 102 of the expansion pin 100 is inserted into the rivet's axial bore through the proximal end thereof and urged thereinto. The slot 90 permits the proximal end of the rivet to expand as the expansion advances into the axial bore. When the circumferential shoulder 104 engages the circumferential shoulder detent 88 in the axial bore, the legs 86a and 86b of the rivet are fully expanded and the expansion pin is locked within the axial bore by the matingly engaged shoulders 88 and 104. A suture may be anchored to the rivet by attachment to the groove 89 on the rivet. The free ends of the suture may be used to attach a substrate to the rivet. As stated above, the extension portion of the expansion pin is preferably metallic. If the portion of the expansion pin 100 to which the extension portion 106 is affixed is bioabsorbable, the extension portion may be separated from the expansion pin by means of a tool adapted to apply tension to the extension portion. If both the extension portion 106 and the body portion 103 of the expansion pin 100 are metallic, it may be preferable to attach the extension portion to the body portion by threaded or breakaway means to facilitate disengagement thereof.

A particularly preferred embodiment of a rivet bone fastener is indicated at 120 in FIGS. 12–14. The rivet 120, shown in distal end view in FIG. 12, includes an expansion pin 150 (FIG. 15) housed within the axial bore which expands the legs of the rivet when rotated 90 degrees. With reference to FIG. 13, the particularly preferred embodiment of a bone rivet 120 in accordance with the present invention, is shown in longitudinal cross-sectional viewed along section line 13—13 of FIG. 12. The rotationally expandable rivet 120 has a proximal end 121, a distal end 122 and a body portion 123 therebetween; the body portion having an axial bore 124 coextensive with the length thereof. The body portion 123 has two or more legs 125 and 126 on the distal end thereof separated by a slot 127. The distal end of the axial bore 128 has an elliptical cross-section as shown in FIG. 12 whereas the remainder of the axial bore 124 has a circular cross-section. A circumferential attachment groove 129 communicates with the proximal end of the rivet through a suture hole 130. In FIG. 12, two opposing detent grooves 131 and 132 are shown, which extend proximally from the elliptical distal end of the axial bore and which are parallel to, and coextensive with the, elliptical bore 128. The purpose of the detent grooves will be discussed below. FIG. 14 illustrates the rivet 120 in proximal end view. The outer edges 140 of the proximal end of the rivet are preferably provided with means operable for preventing rotation of the rivet when a torque is applied to the rivet.

A rotatable expansion pin 150 adapted for expansion of the rivet 120 is illustrated in elevational view in FIG. 15 and in distal end view in FIG. 16. The expansion pin 150 has a proximal end 152, a distal end 151 and a shaft portion 153 therebetween. The proximal end 152 of the pin 150 is most preferably square, having four flat orthogonal sides 154 thereon which provide means operable for receiving a tool such as, for example, a wrench, for rotating the pin 150 within the axial bore 124 of the rivet 120. The distal end 151 of the expansion pin 150 is substantially elliptical in cross-section; having a dimension along a major axis A and a minor axis B (FIG. 16) equal to or slightly less than the corresponding dimensions of the elliptical distal end 128 of the axial bore in the rivet 120. The distal end 151 of the expansion pin 150 preferably includes at least one, and more preferably two, protuberances 161 and 162 extending laterally therefrom along the major axis A. The protuberances 161 and 162 are dimensioned to matingly engage the grooves 131 and 132 in the axial bore 124 of the rivet 120 when the legs 125 and 126 are expanded. The expansion pin 150 preferably includes a circumferential breakaway joint 155 proximal to the elliptical distal end 152 of the pin 150. The expansion pin 150 is rotationally disposed within the axial bore 124 of the rivet 120.

In operation, as with the previous rivet bone fasteners, a hole must be drilled into the bone at a desired attachment site. The rivet 120, with the expansion pin 150 rotatably mounted within the rivet's axial bore, is inserted into the hole and advanced thereinto until the expandable legs of the rivet are completely within the hole. While preventing the rivet from turning by employing suitable fixation means such as grasping the proximal end thereof with a tool, the expansion pin 150 is rotated 90 degrees, bringing the major axis of the elliptical distal end of the pin into alignment with the minor axis of the elliptical portion of the axial bore. Further rotation of the pin is resisted when the major axis of the pin intersects the detent grooves adjacent to the elliptical portion of the axial bore. At this point of rotation, the legs of the rivet are fully expanded to engage the bone. The mid-portion of a length of suture may then be pressed into the circumferential groove 129 at the proximal end of the rivet and the free ends of the suture threaded through the hole 130. With the suture anchored to the rivet, the suture may then be used to attach a substrate such as, for example, soft tissue to the rivet. The rivet and the expansion pin, or portions thereof, may be fabricated from any biocompatible material, including both absorbable and non-absorbable.

In the case of both union and non-union bone fractures, when the segments of bone comprising the fracture site are juxtaposed, healing is accelerated by applying a compressive force to the fracture site. Prior art teaches the use of a bone plate, together with one or more screws, to provide a compressive force to a fracture site in order to stabilize the fracture site and accelerate healing. In this procedure, a pilot hole is first drilled through both sections of the fractured bone comprising the fracture site. The pilot hole in the proximal section of the fractured bone is then enlarged, and the distal portion of the pilot hole tapped to matingly engage the screw thread. A bone plate is fastened to the bone by means of the screw and the screw advanced into the tapped pilot hole until the bone plate compresses the fracture site. This technique is time consuming and there may be occasions when access to the screw head, in order to apply a torque thereto, is obstructed by another anatomical structure. In such a case, it may not be possible to apply the desired compressive force.

Turning now to FIG. 17, an alternative method, in accordance with the present invention, for applying a compressive force to a fracture site employs the use of a compression rivet 170. The compression rivet 170 has a distal end 171 comprised of at least two expandable legs 172 and 173, an axial bore 174, and a proximal end 175 having ratcheting means 176 on the outer surface thereof. The compression rivet 170 includes a bone insertion portion 177 and a ratcheting portion 178. The bone insertion portion 177 of the rivet 170 may be configured in accordance with any of the embodiments of a rivet bone fasteners 10, 70 or 120, discussed earlier, using their respective expansion pins 40, 100 and 150 to expand the legs thereof. The proximal ratcheting portion 178 of the compression rivet is, however, absent in the rivet bone fasteners discussed previously. The ratcheting portion 178 includes ratcheting means, such as, for example, a plurality of annular grooves 176 circumscribing the ratcheting portion 178 of the compression rivet.

In order to use the compression rivet 170 to stabilize and compress a fracture site, the site is first exposed as illustrated in FIG. 18. The segments of bone 180 and 181 are brought into juxtaposition and a hole 182 is drilled. The distal bone insertion portion 177 of the compression rivet is then inserted into the hole, and the legs 172 and 173 expanded by means an expansion pin operable for performing this function. A washer 190, shown in top view in FIG. 19, and cross-sectional view in FIG. 20, having a central aperture 191 and a plurality of flanges 192 projecting into the aperture, is advanced in a distal direction along the ratcheting portion 178 by means of pressure thereon exerted by a suitable tool (not shown). When the bone-facing surface 183 of the washer 190 abuts the bone 181, and can be advanced no further, the bone segments 181 and 182 are both stabilized and held in juxtaposition along the fracture line 184 by a compressive force exerted by the washer 190. The flanges 192 on the washer lockingly engage the racheting means 176 on the outer surface of the ratcheting portion 178 of the rivet 170 thereby preventing the washer from moving in a distal direction. The washer compresses the fractured portions of bone against one another thereby accelerating the fracture healing process.

Figure 21:
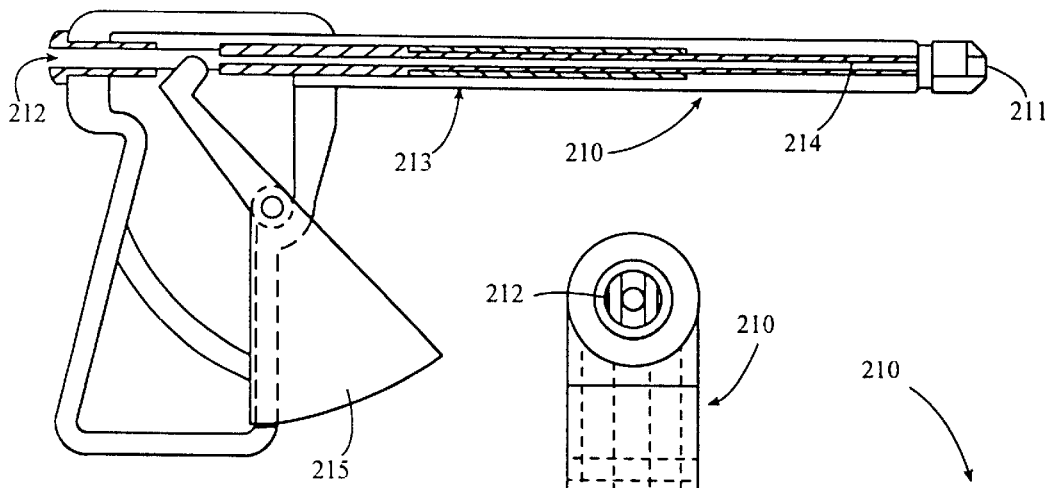
FIG. 21 is a partially cutaway elevational view of a rivet insertion tool adapted for inserting a top loading rivet into a hole drilled in bone and forcing a top loading expansion pin into the axial bore of the rivet to expand the legs of the rivet.
Figure 22:
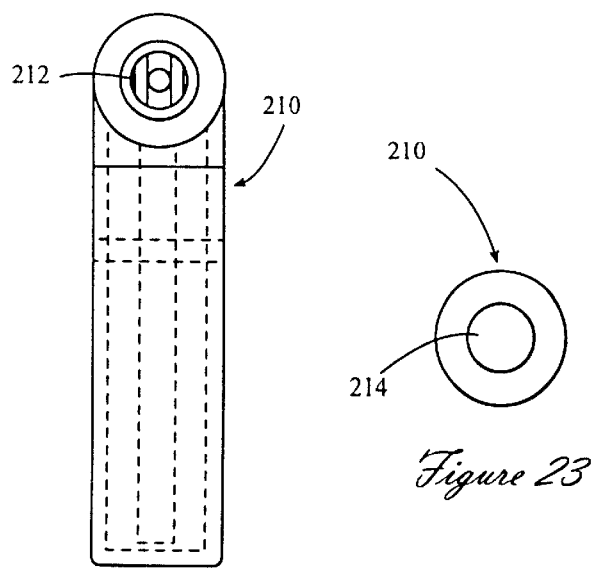
FIG. 22 is a schematic left end view of the rivet insertion tool of FIG. 21.
Figure 23:
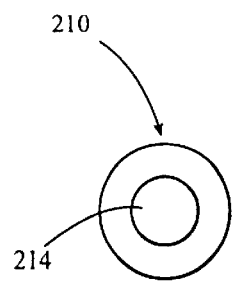
FIG. 23 is a right end view of the rivet insertion tool of FIG. 21.
Figure 24:
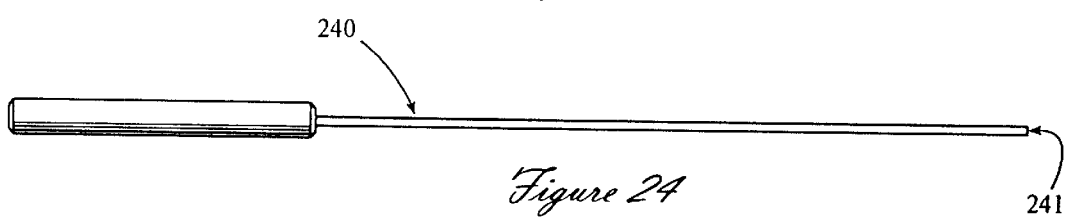
FIG. 24 is a side elevational view of an expansion pin insertion rod adapted for use with the rivet insertion tool of FIG. 21.

A tool useful for inserting a top-loading rivet in accordance with the present invention into a hole drilled in a bone is shown in elevational cross-sectional view at 210 in FIG. 21 and front and rear end views in FIGS. 22 and 23 respectively. The tool 210 has a distal rivet grasping end 211 and a proximal end 212 and a barrel 213 therebetween having an axial bore 214. With the proximal end 81 of the top-loading rivet 70 held securely within the distal end 211 of the tool 170 by suitable rivet grasping means, the distal end 82 of the rivet bone fastener is inserted into a hole drilled in a bone. The distal end 241 of a plunger 240 (FIG. 24) is inserted into the proximal end 212 of the barrel 214 and advanced until the distal end 241 is in contact with the proximal end 101 of the expansion pin 100. Squeezing rotatably mounted trigger 215 forces the expansion pin 100 into the axial bore 84 of the top-loading rivet 70 thereby expanding the legs 86a and 86b thereof to press against the surrounding bone. The proximal end 81 of the rivet 70 is released when the trigger 215 returns to its initial position. As discussed earlier, in the event that the body portion 103 of the expansion pin 100 is bioabsorbable and the extension portion 106 is metallic, the tool 210 further includes means adapted to apply tension to the extension portion, following leg expansion, in a quantity sufficient to separate the extension portion 106 from the body portion 103.

While particular embodiments of the present invention have been illustrated and described, it would be obvious to those skilled in the art that various other changes and modifications can be made without departing from the spirit and scope of the invention. For example, the distal end 151, while preferably elliptical in cross-section, can be made in a variety of geometries, any of which will force the legs of the rivet to expand when the expansion pin is rotated through an angle. The essential element of the rivet 120 and the rotational expansion pin 150 is that the legs of the rivet are expanded by rotating the pin. It is therefore intended to cover in the appended claims all such changes and modifications that are within the scope of this invention.

What I claim is:

1. A rivet bone fastener for fixation within a hole drilled in a bone comprising:
    (a) a rivet having a proximal end, a distal end and an elongate body portion therebetween, said body portion having a length, and an axial bore coextensive with said length, said axial bore comprising a non-cylindrical distal portion and a cylindrical proximal portion, said body portion having a plurality of expandable legs disposed adjacent to said non-cylindrical distal portion of said axial bore;
    (b) an expansion pin having a cylindrical proximal end and a non-cylindrical distal end, rotatably mounted within said axial bore, and wherein rotation of said expansion pin within said axial bore expands said expandable legs of said rivet outwardly.

2. The rivet bone fastener in accordance with claim 1 wherein said rivet further comprises substrate fastening means affixed thereto, said substrate fastening means being operable for attaching a substrate to said rivet.

3. The rivet bone fastener in accordance with claim 1 wherein said expansion pin further comprises substrate fastening means affixed thereto, said substrate fastening means being operable for attaching a substrate to said rivet.

4. The rivet bone fastener in accordance with claim 1 wherein said rivet is bioabsorbable.

5. The rivet bone fastener in accordance with claim 1 wherein said expansion pin is bioabsorbable.

6. The rivet bone fastener in accordance with claim 1 wherein said proximal cylindrical portion of said expansion pin further comprises rotation means integral therewith, said rotation means being adapted to receive a tool operable for rotating said expansion pin.

7. The rivet bone fastener in accordance with claim 2 wherein said proximal cylindrical portion of said expansion pin further comprises rotation means integral therewith, said rotation means being adapted to receive a tool operable for rotating said expansion pin.

8. The rivet bone fastener in accordance with claim 3 wherein said proximal cylindrical portion of said expansion pin further comprises rotation means integral therewith, said rotation means being adapted to receive a tool operable for rotating said expansion pin.

9. The rivet bone fastener in accordance with claim 1 wherein said non-cylindrical portion of said expansion pin and said non-cylindrical distal portion of said axial bore have an elliptical cross-section when viewed in the direction of the axial bore.

10. The rivet bone fastener in accordance with claim 2 wherein said substrate fastening means is a suture.

11. The rivet bone fastener in accordance with claim 3 wherein said substrate fastening means is a suture.

12. The rivet bone fastener in accordance with claim 2 wherein said proximal cylindrical portion of said expansion pin further comprises rotation means integral therewith, said rotation means being adapted to receive a tool operable for rotating said expansion pin.

13. The rivet bone fastener in accordance with claim 2 wherein said non-cylindrical portion of said expansion pin and said non-cylindrical distal portion of said axial bore have an elliptical cross-section when viewed in the direction of the axial bore.

14. A rivet bone fastener for fixation within a hole drilled in a bone comprising:
    (a) a rivet having a proximal end, a distal end and an elongate body portion therebetween, said body portion having a length, and an axial bore coextensive with said length, said axial bore defining an axial bore direction, said axial bore comprising a elliptical distal portion and a cylindrical proximal portion, said body portion having a plurality of expandable legs disposed adjacent to said elliptical distal portion of said axial bore;
    (b) a rotational expansion pin having a cylindrical proximal end and a non-cylindrical distal end, rotatably mounted within said axial bore, and wherein rotation of said expansion pin within said axial bore expands said expandable legs of said rivet outwardly;
    (c) rotational detent means disposed on a inner axial bore-facing surface of said expandable legs operable for engaging said elliptical distal portion of said expansion pin when said expandable legs are fully expanded to resist further rotation of said rotational expansion pin.

* * * * *